(12) United States Patent
Bouduban et al.

(10) Patent No.: US 12,121,249 B2
(45) Date of Patent: *Oct. 22, 2024

(54) METHODS AND SYSTEMS FOR PREPARING BONE FOR A SURGICAL PROCEDURE

(71) Applicant: Medos International Sarl, Le Locle (CH)

(72) Inventors: Nicolas Bouduban, Bruegg (CH); Patrick Burki, Solothurn (CH); Laurent Lafosse, Sevrier (FR)

(73) Assignee: Medos International Sarl, Le Locle (CH)

( * ) Notice: Subject to any disclaimer, the term of this patent is extended or adjusted under 35 U.S.C. 154(b) by 256 days.

This patent is subject to a terminal disclaimer.

(21) Appl. No.: 17/734,528

(22) Filed: May 2, 2022

(65) Prior Publication Data
US 2022/0280170 A1 Sep. 8, 2022

Related U.S. Application Data

(63) Continuation of application No. 16/432,027, filed on Jun. 5, 2019, now Pat. No. 11,344,323, which is a
(Continued)

(51) Int. Cl.
*A61B 17/17* (2006.01)
*A61B 17/88* (2006.01)

(52) U.S. Cl.
CPC ...... *A61B 17/1778* (2016.11); *A61B 17/1796* (2013.01); *A61B 17/8897* (2013.01)

(58) Field of Classification Search
CPC . A61B 17/17; A61B 17/1778; A61B 17/1796; A61B 17/1739; A61B 17/1714; A61B 17/88; A61B 17/8897
See application file for complete search history.

(56) References Cited

U.S. PATENT DOCUMENTS 5,026,376 A 6/1991 Greenberg
5,141,513 A 8/1992 Fortune et al.
(Continued)

FOREIGN PATENT DOCUMENTS

CN 1870944 A 11/2006
CN 1925799 A 3/2007
(Continued)

OTHER PUBLICATIONS

Burns et al., "Anterior Stabilization of the Shoulder: latarjet Protocol," brighamandwomens.org Mar. 2009. <http://www.brighamandwomens.org/Patients_Visitors/pcs/rehabilitationservices/Physical-Therapy-Standards-of-Care-and-Protocols/Shoulder%20-%20Latarjet%20Protocol.pdf> Last accessed Mar. 16, 2016. 10 Pages.
(Continued)

*Primary Examiner* — Christopher J Beccia
(74) *Attorney, Agent, or Firm* — Mintz Levin Cohn Ferris Glovsky and Popeo, P.C.

(57) ABSTRACT

Systems and methods for preparing a bone for a surgical procedure are provided. In general, the described techniques use a surgical guide device including a cannula having first and second parallel elongate channels adjacent to one another, and first and second elongate sleeves configured to be removably and replaceably received in the first and second channels, respectively. The first sleeve has a plurality of openings formed therein, each being in communication with a respective wire-receiving lumen extending through the first sleeve. Each of the openings defines a different offset distance between the wire-receiving lumen in communication with that opening and a wire-receiving lumen extending through the second sleeve. The surgical device can be manipulated so as to define positions of first and second openings in a bone, such as a glenoid or other bone,
(Continued)

to receive bone screws or other elements for attaching a bone graft to the bone.

20 Claims, 12 Drawing Sheets

Related U.S. Application Data continuation of application No. 14/983,383, filed on Dec. 29, 2015, now Pat. No. 10,327,789.

(56) References Cited

U.S. PATENT DOCUMENTS

| | | | |
|---|---|---|---|
| 5,147,367 A | 9/1992 | Ellis | |
| 5,207,753 A | 5/1993 | Badrinath | |
| 5,250,055 A | 10/1993 | Moore et al. | |
| 5,320,626 A | 6/1994 | Schmieding | |
| 5,324,295 A * | 6/1994 | Shapiro | A61B 17/1714 606/86 R |
| D357,534 S | 4/1995 | Hayes | |
| 5,409,493 A | 4/1995 | Greenberg | |
| 5,445,642 A | 8/1995 | McNulty et al. | |
| 5,531,751 A | 7/1996 | Schultheiss et al. | |
| 5,700,266 A | 12/1997 | Harryman, II | |
| 5,746,743 A | 5/1998 | Greenberg | |
| 5,836,950 A | 11/1998 | Hansson | |
| 5,961,530 A | 10/1999 | Moore et al. | |
| 5,976,145 A | 11/1999 | Kennefick, III | |
| D433,506 S | 11/2000 | Asfora | |
| 6,358,253 B1 | 3/2002 | Torrie et al. | |
| 6,673,115 B2 | 1/2004 | Resch et al. | |
| 6,878,150 B1 | 4/2005 | McGuire et al. | |
| 7,204,839 B2 | 4/2007 | Dreyfuss et al. | |
| 7,736,364 B2 | 6/2010 | Stone | |
| 8,257,359 B2 | 9/2012 | Burkhart et al. | |
| 8,273,091 B2 | 9/2012 | Elghazaly | |
| 8,308,732 B2 | 11/2012 | Millett et al. | |
| 8,449,543 B2 | 5/2013 | Pool et al. | |
| 8,506,573 B2 | 8/2013 | Dreyfuss et al. | |
| 8,617,219 B2 | 12/2013 | Oren et al. | |
| 8,771,279 B2 | 7/2014 | Philippon et al. | |
| 8,956,369 B2 | 2/2015 | Millett et al. | |
| 10,327,789 B2 * | 6/2019 | Bouduban | A61B 17/1778 |
| 11,344,323 B2 | 5/2022 | Bouduban et al. | |
| 2003/0078584 A1 | 4/2003 | Tipirneni | |
| 2008/0275453 A1 | 11/2008 | Lafosse et al. | |
| 2009/0198171 A1 | 8/2009 | Kleinekofort et al. | |
| 2009/0202387 A1 | 8/2009 | Dlugos, Jr. et al. | |
| 2010/0137889 A1 | 6/2010 | Oren et al. | |
| 2011/0208198 A1 | 8/2011 | Anderson et al. | |
| 2011/0213375 A1 * | 9/2011 | Sikora | A61B 17/1764 606/87 |
| 2011/0251621 A1 | 10/2011 | Sluss et al. | |
| 2011/0270255 A1 | 11/2011 | Smith | |
| 2011/0295252 A1 * | 12/2011 | Tipirneni | A61B 17/861 606/62 |
| 2012/0136357 A1 | 5/2012 | Torrie et al. | |
| 2012/0253353 A1 * | 10/2012 | McBride | A61B 17/1757 606/97 |
| 2012/0296338 A1 | 11/2012 | Burkhart et al. | |
| 2013/0066371 A1 | 3/2013 | Rogers et al. | |
| 2013/0238099 A1 | 9/2013 | Hardy et al. | |
| 2014/0081281 A1 | 3/2014 | Felder | |
| 2014/0114317 A1 | 4/2014 | Oren et al. | |
| 2014/0276892 A1 | 9/2014 | Pakzaban et al. | |
| 2016/0106491 A1 | 4/2016 | Zhang et al. | |

FOREIGN PATENT DOCUMENTS

| | | |
|---|---|---|
| CN | 103037816 A | 4/2013 |
| CN | 103860292 A | 6/2014 |
| CN | 104159625 A | 11/2014 |
| CN | 104853685 A | 8/2015 |
| DE | 102006027054 A1 | 12/2007 |
| JP | 2012105927 A | 6/2012 |
| JP | 2015531654 A | 11/2015 |
| WO | WO-2005011478 A2 | 2/2005 |
| WO | WO-2005025431 A1 | 3/2005 |
| WO | WO-2008015670 A2 | 2/2008 |
| WO | WO-2008066756 A2 | 6/2008 |
| WO | WO-2011119884 A1 | 9/2011 |
| WO | WO-2013098806 A1 | 7/2013 |
| WO | WO-2014078709 A1 | 5/2014 |
| WO | WO-2015139550 A1 | 9/2015 |

OTHER PUBLICATIONS

DePuy Mitek, "Bristow-Latarjet Instability Shoulder System," Depuysynthes.com 2011. <http://synthes.vo.Ilnwd.net/o16/LLNWMB8/US%20Mobile/Synthes%20North%20America/Product%20Support%20Materials/Technique%20Guides/CA6659%20Mitek_Latarjet_Surgical_Technique-FINAL.pdf> Last Accessed Mar. 16, 2016. 32 Pages.

European Search Report for Application No. 16207083.3 dated May 9, 2017.

* cited by examiner

METHODS AND SYSTEMS FOR PREPARING BONE FOR A SURGICAL PROCEDURE

CROSS REFERENCE TO RELATED APPLICATIONS

The present application is a continuation of U.S. patent application Ser. No. 16/432,027 (now U.S. Pat. No. 11,344,323) entitled "Methods And Systems For A Bone Preparation For A Surgical Procedure" filed Jun. 5, 2019, which is a continuation of U.S. patent application Ser. No 14/983,383 (now U.S. Pat. No. 10,327,789) entitled "Methods And Systems For A Bone Preparation For A Surgical Procedure" filed Dec. 29, 2015, which is hereby incorporated by reference in its entirety.

FIELD

The present disclosure relates to methods and systems for a bone preparation for a surgical procedure.

BACKGROUND

The shoulder joint has the largest range of motion of any joint in the human body. It is a ball-and-socket joint having three bones: a shoulder blade (scapula), a collarbone (clavicle), and an upper arm bone (humerus). A rounded head of the upper arm bone (humeral head) fits into a shallow socket in the shoulder blade called a glenoid. The humeral head is usually much larger than the glenoid, and together they have little inherent stability. The shoulder joint is thus prone to instability and dislocation. A soil fibrous tissue rim called a labrum surrounds the glenoid to form a cup for the humeral head to move within the glenoid. The labrum thus helps maintain stability of the shoulder, while allowing for a very wide range of motion. When the labrum of the shoulder joint is damaged, the stability of the shoulder joint is compromised, leading to subluxation and dislocation of the joint. Recurrent dislocations may cause damage to the bones of the joint—the humeral head and the glenoid. In particular, damage to the anterior-inferior part of the glenoid will cause a decrease in the area of contact with the humeral head.

Surgical procedures intended to address the shoulder instability are typically divided into soft tissue and bony procedures. Surgical reconstruction targeting the shoulder joint's soft tissues (which typically involves labral repairs) can be adequate to address certain shoulder instability problems. However, in cases where significant bone deficiency is present (e.g., when greater than 20% of the glenoid's surface area is missing), addressing only the soft tissue issues is typically not sufficient. Bone deficiency can result from trauma, overuse, congenital deformity, or recurrent dislocation.

Reestablishment of shoulder stability requires recognition and treatment of bone defects. When bone deficiencies or lesions reach certain dimensions, reconstruction of these deficits is typically performed using a bone graft. Although existing techniques have been used with some success, the bone graft may not be properly aligned with the glenoid or other bone structure being reconstructed. In particular, when the bone to be reconstructed is being prepared for receiving the graft, it may be challenging to identify proper locations for attachment elements (e.g., screws) that are to be inserted into the bone when the graft is attached thereto.

Accordingly, there is a need for improved techniques and devices for preparing a bone for a surgical procedure, such as a procedure involving use of a bone graft.

SUMMARY

In some aspects, a surgical guide device is provided that includes a cannula comprising first and second parallel elongate channels positioned adjacent to one another, a first elongate sleeve configured to be removably and replaceably received in the first channel, and a second elongate sleeve configured to be removably and replaceably received in the second channel. The first sleeve has a proximal housing configured to protrude from a proximal end of the cannula, and the proximal housing of the first sleeve has a plurality of openings formed therein, each opening being in communication with a respective wire-receiving lumen that extends through the first elongate sleeve to a distal end thereof. The second sleeve has a proximal end configured to protrude from the proximal end of the cannula when the second sleeve is positioned therein, the second sleeve having a wire-receiving lumen extending therethrough.

The surgical guide device can vary in any number of ways. For example, the surgical guide device can further include a coupling element configured to couple the first sleeve to the second sleeve so as to prevent rotation of the first and second sleeves with respect to one another.

In some embodiments the cannula extends from a proximal handle. The proximal handle can be non-removably coupled to the cannula. The first and second parallel elongate channels can be discrete and separate channels.

The first and second elongate sleeves can have a number of different configurations. For example, in some embodiments, the plurality of openings formed in the first sleeve can include three openings. Each of the three openings can define a different offset distance between the wire-receiving lumen in communication with the opening and the wire-receiving lumen extending through the second elongate sleeve.

The first and second elongate sleeves can be removably and replaceably disposed in the first and second elongate channels via a clearance fit. The second elongate sleeve can extend more proximally beyond a proximal end of the cannula than the first elongate sleeve. For another example, the housing of the first sleeve can be an elongate tubular housing having a diameter that is larger than a diameter of an opening leading to the first channel of the cannula. In at least some embodiments, the proximal end of the first sleeve has a washer-like shape. In at least some embodiments, a distal end of the second sleeve has a threaded portion.

The distal end of the first sleeve can be configured to extend beyond a distal end of the cannula when the first sleeve is positioned therein. A distal end of the second sleeve can be configured to extend beyond a distal end of the cannula when the second sleeve is positioned therein.

In some aspects, a method for preparing a bone for a surgical procedure is provided that includes positioning a cannula having first and second parallel elongate channels adjacent to one another along an end surface of the bone such that the first and second parallel elongate channels are disposed in a first plane, positioning a first wire in the first channel such that the first wire extends along a plane defined by the end surface of the bone, and positioning a second wire in the second channel and inserting a distal end of the second wire into a portion of the bone spaced away from the end surface to define a first opening in the bone. The method further includes at least partially retracting the first wire from the first channel and rotating the cannula about the second wire while the second wire remains in place, and, after the cannula is rotated, inserting the first wire through the bone to define a second opening in the bone.

The method can vary in any number of ways. For example, the first wire can be inserted into the cannula through a first elongate sleeve disposed in the cannula, and the second wire can be inserted into the cannula through a second elongate sleeve disposed in the cannula. For another example, the method can further include inserting the second wire into the bone to an increased depth.

In some embodiments, the cannula can be rotated about the second wire such that the first and second parallel elongate channels are disposed in a second plane that is substantially perpendicular to the first plane.

In some embodiments, the method further includes attaching a bone graft to the bone using first and second screws, the first screw extending through the bone graft and into the first opening in the bone, and the second screw extending through the bone graft and into the second opening in the bone.

The bone can be a glenoid or other bone structure.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1A:
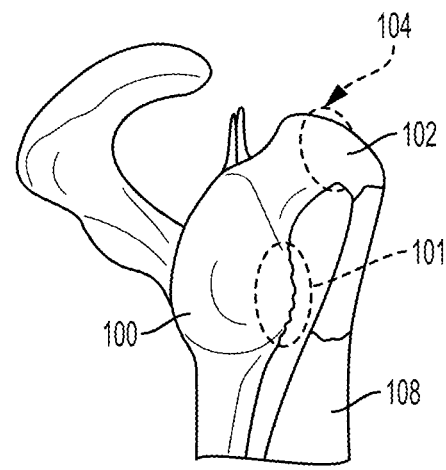
FIG. 1A is a perspective view of a portion of a shoulder joint, showing a glenoid and an intact coracoid.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to systems and methods for preparing a bone for a surgical procedure, and for properly mating a bone graft to the base bone in a manner that enables the graft to be flush when mounted to the base bone. The bone can be, for example, a glenoid or other bone structure. The bone is prepared so that it can receive a graft that compensates for certain deficiency in the bone. For example, in a glenoid reconstruction procedure, the glenoid with some degree of bone deficit and associated loss of shoulder stability can have a bone graft attached thereto to treat the shoulder instability. To prepare the bone, positions of openings in the bone, which will receive therein bone screws or other attachment elements that attach the graft to be bone, are defined. In the described embodiments, the openings are defined in a straightforward and simplified manner, such that, unlike in conventional approaches, the outcome of the surgical procedure becomes less dependent on a surgeon's experience. A likelihood of patient's inconvenience and damage to the surgical site is thus greatly reduced.

To define the openings in the bone, the described techniques use a surgical guide device including a cannula having a handle coupled thereto that allows manipulating the cannula. The cannula has first and second parallel elongate channels extending therethrough adjacent to one another. The surgical guide device also includes first and second elongate sleeves configured to be removably and replaceably received in the first and second elongate channels, respectively. The first and second elongate sleeves are typically fully cannulated such that they can receive wires (e.g., K-wires) in their wire-receiving lumens extending therethrough.

The first elongate sleeve has, at a proximal end thereof, a plurality of openings formed therein, each of which leads to a respective wire-receiving lumen or channel that extends through the first elongate sleeve to a distal end thereof. Three or other number of openings can be formed at the proximal end of the first elongate sleeve. Each of the openings defines a different offset distance between the wire-receiving lumen in communication with that opening and a wire-receiving lumen extending through the second elongate sleeve. The offset distance, in turn, defines an offset distance of openings to be formed in the bone from a certain portion of the bone, such as an end surface of the bone. For example, when the bone is a glenoid, the openings are defined in a glenoid rim at a predefined offset distance from the edge of the glenoid rim.

During preparation of a bone for a surgical procedure, the cannula is first positioned along an end surface of the bone such that the first and second elongate channels in the cannula are disposed in a first plane. A desired offset distance is then selected, which is done by positioning a first wire in one of the plurality of openings in the first sleeve, the opening leading to a corresponding wire-receiving lumen in the first sleeve. When the first wire is inserted into the cannula in this manner, the opening in the first sleeve of the cannula is aligned with the end surface of the bone. A second wire is then inserted into the second sleeve and advanced into the bone to define a first opening in the bone. The first wire is then at least partially retracted from the first channel (e.g., it can be removed from the first channel) to allow the cannula to be manipulated. In the illustrated embodiments, the cannula is rotated about the second wire while the second wire remains in place (inserted in the bone). As a result of the rotation of the cannula, the position of the first channel with respect to the bone is changed such that both the first and second channels can be disposed in a second plane that is substantially perpendicular to the first plane. After that, the first wire is again inserted into the first channel to define a second opening in the bone.

Figure 1B:
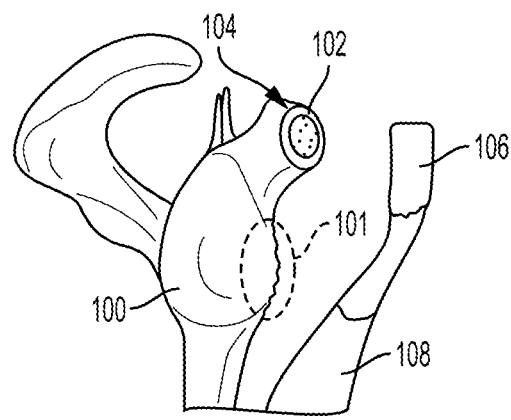
FIG. 1B is a perspective view of the portion of the shoulder joint of FIG. 1A, showing a bone graft created by cutting off a portion of the coracoid.
Figure 1C:
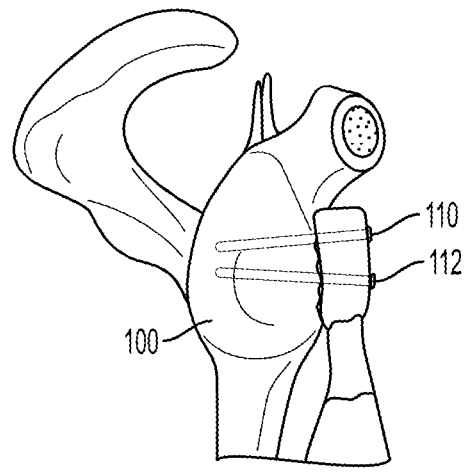
FIG. 1C is a perspective view of the portion of the shoulder joint of FIG. 1B, illustrating generally a Latarjet procedure used to attach the bone graft to the glenoid.

The techniques described herein can be used to prepare a bone for a variety of different surgeries. Among various bone reconstruction procedures to correct a bone defect or fracture, the Latarjet procedure is a commonly used procedure involving removal and transfer of a portion of a coracoid bone, or coracoid, to the anterior glenoid. The Latarjet procedure is used to repair an anterior shoulder dislocation or erosion of the shoulder joint, and prevent further loss of bone. The placement of the coracoid acts as a bone bloc or graft, which, combined with the transferred muscles acting as a strut, increases stability of the shoulder joint and thus prevents its further dislocation. FIGS. 1A, 1B, and 1C illustrate generally a Latarjet procedure for reconstruction of a bone deficiency in a glenoid 100. It should be appreciated that only a portion of a shoulder is shown in FIGS. 1A-1C.

The glenoid 100 can have a bone defect in an area 101 thereof, which is identified in FIGS. 1A and 1B. The coracoacromial ligament and the pectoralis minor attachment are divided, whereas coracobrachialis and the short head of the biceps origins remain intact. A coracoid 102 is osteotomized at a level of its "knee" 104 so as to form a bone graft 106, as schematically shown in FIGS. 1A and 1B. As also shown, a conjoined tendon 108 remains attached to the coracoid bone graft 106. The bone graft 106 can be prepared for bone reconstruction using suitable techniques as known in the art. For example, it can be shaped and contoured to fill the bone defect in the area 101 of the glenoid 100.

To increase the bone area of the glenoid 100, the appropriately prepared bone graft 106 is then attached to the glenoid 100, as shown in FIG. 1C where the glenoid 100 is shown at least partially transparent for illustration purposes only. As FIG. 1C illustrates, the bone graft 106 can be attached to the glenoid 100 using screws 110, 112 that are inserted at the anterior rim of the glenoid 100. The coracoid bone graft 106 thus fills the bone deficiency of the glenoid 100, and the conjoined tendon 108 provides a sling effect, stabilizing the shoulder.

Figure 2:
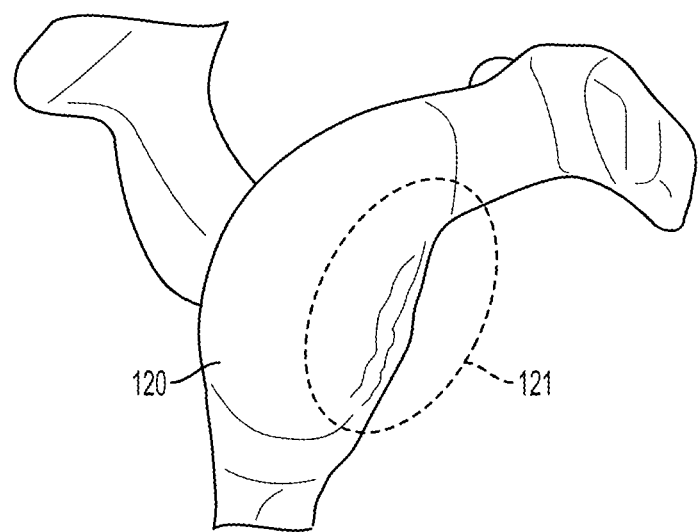
FIG. 2 is a perspective view of a glenoid with a bone deficit.
Figure 3:
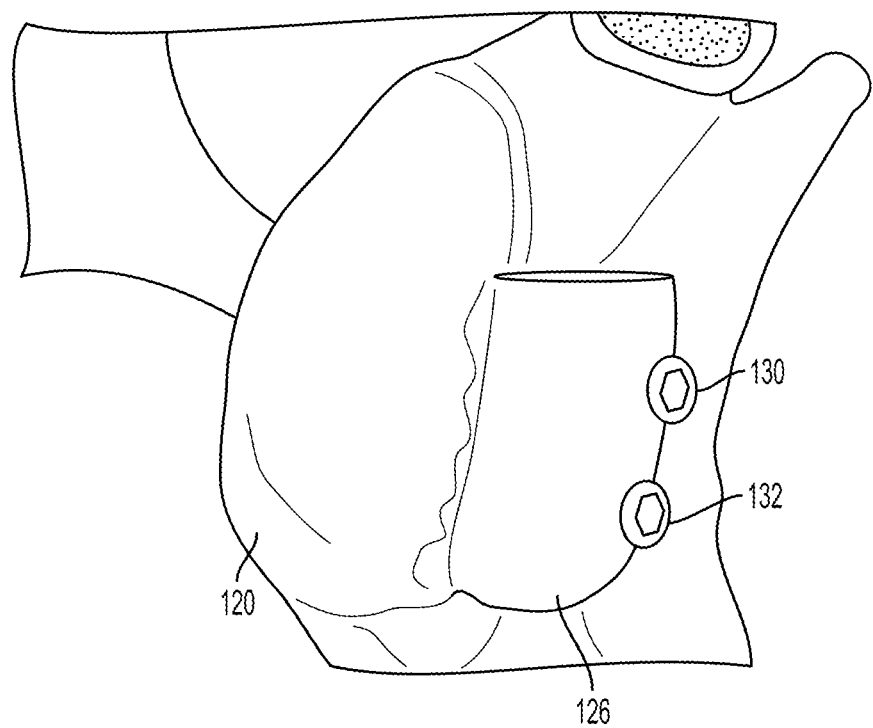
FIG. 3 is a perspective view of the glenoid of FIG. 2, showing a bone graft attached to the glenoid to compensate for the bone deficit.

FIGS. 2 and 3 additionally illustrate an example of a glenoid 120 having an area 121 with a bone defect which can be compensated for by attaching a bone graft 126 to the rim of the glenoid 120 using first and second screws 130, 132.

During a Latarjet surgery, the ability to reliably position the coracoid bone graft adjacent to the glenoid such that the graft is flush with the glenoid surface depends on the skill and experience of a surgeon performing the procedure. For example, instead of being positioned flush with the glenoid's surface, the bone graft can be placed medially or laterally removed from the glenoid rim. However, if the bone graft is disposed too medially from the glenoid rim, there may be a high likelihood that the surgical procedure will not adequately correct the instability of the shoulder. On the other hand, if the bone graft is disposed too laterally of the glenoid rim, the humeral head will touch the bone graft which can lead to damage to the cartilage. As another highly undesirable consequence, if the surface of the bone graft is not parallel to the glenoid surface, a screw may be inserted into the joint rather than into the glenoid, which can cause severe bone damage.

Accordingly, the described devices and techniques provide a way to position a bone graft adjacent to a bone structure with a bone deficiency in a more precise and simplified manner. More specifically, the described devices and techniques provide a way to prepare a bone for a surgical procedure involving attachment of a bone graft to the bone. Thus, techniques are provided for preparing a glenoid to receive a coracoid bone graft as part of a glenoid bone reconstruction procedure. Referring back to FIGS. 2 and 3, these techniques allow alignment of the bone graft 126 with the surface of the glenoid 120 to be accomplished in a reliable and straightforward manner. The outcome of the procedure is thus less dependent on the level of skill and experience of a surgeon, which can improve the success and efficiency of the surgery. It should be appreciated that, while the techniques presented herein are described in connection with a glenoid bone reconstruction procedure, other bone structures can be prepared for bone reconstruction procedures using the devices and methods in accordance with such techniques.

As mentioned above, a bone graft can be attached to a bone to compensate for a bone deficit using first and second screws, such as, for example, screws 110, 112 in FIG. 1C or screws 130, 132 in FIG. 3. To properly align the bone graft with the bone such that their surfaces are flush with one another, the bone graft and the screws that secure it should be positioned at an appropriate offset with respect to the bone. Thus, during a glenoid reconstruction, the coracoid bone graft must be placed at an appropriate offset from the glenoid rim. It is therefore necessary to determine proper locations for holes or openings in the glenoid that receive the bone screws used to attached the bone graft to the glenoid.

FIGS. 4A, 4B, 5, 6, 7A, 7BV, 7C, 8A, and 8B illustrate surgical guide instruments that can be used to determine and effect the proper positioning of first and second openings in the glenoid in accordance with the present disclosure. The locations of the openings are defined using a surgical guide device configured to receive therethrough elongate wires, such as K-wires or other temporary fixation elements, as discussed below. The surgical guide instruments described herein allow preparation of a bone for a surgical procedure such that a graft can later be attached to the prepared bone while the graft is positioned flush with the bone. It should be noted, that, as used herein, the term "flush" means that the graft's surface will be substantially aligned with the bone's surface. The anatomy of the bone and/or configuration of the graft can be such that their surfaces are curved and not flat throughout. Also, a certain offset between the surfaces of the bone and the graft is permissible, as long as the alignment is sufficient to provide stability to the site being reconstructed and without damaging anatomical structures involved.

Figure 4A:
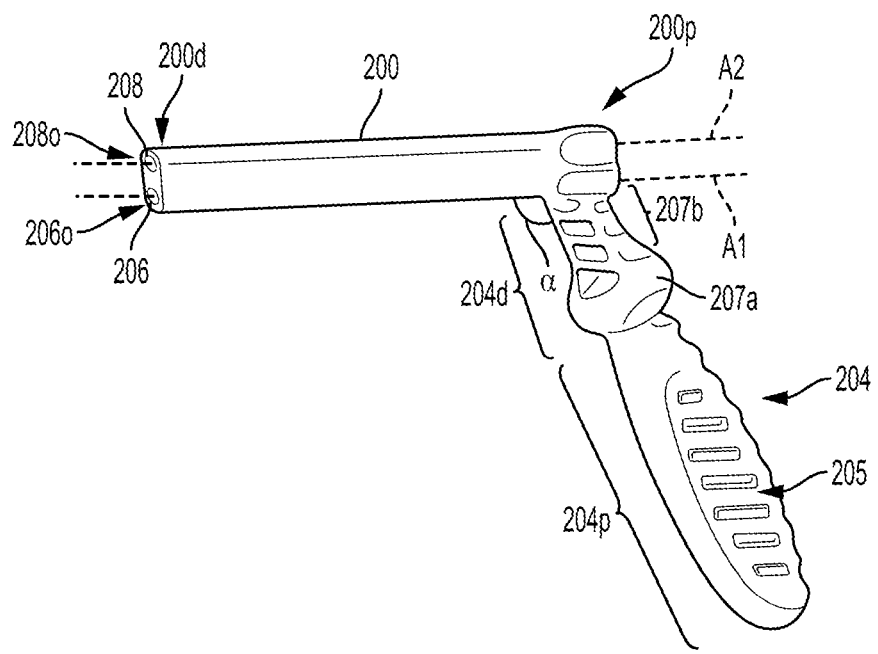
FIG. 4A is a perspective view of one embodiment of a cannula having first and second elongate channels, and a handle coupled to the cannula.
Figure 4B:
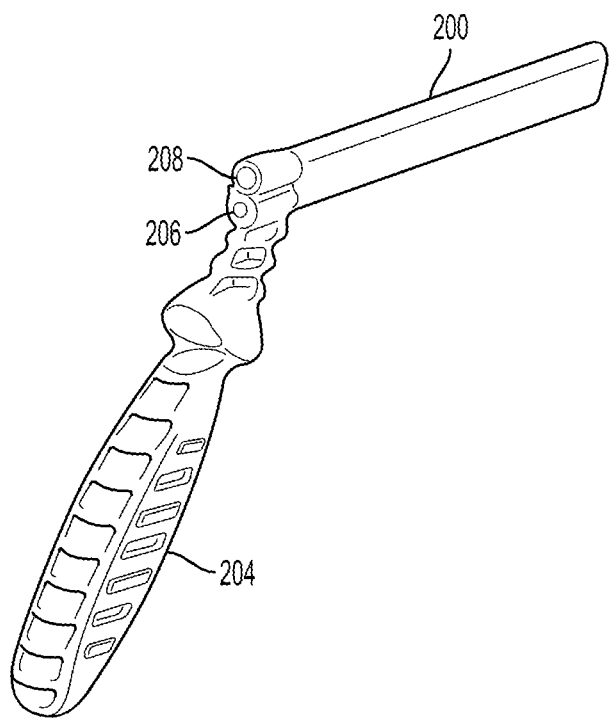
FIG. 4B is another perspective view of the cannula of FIG. 4A.

A surgical guide device can include a cannula, one embodiment of which is shown in FIGS. 4A and 4B. As illustrated, a cannula 200 having proximal and distal ends 200p, 200d is in the form of an elongate tubular body with its proximal end 200p extending from a proximal handle 204. The cannula 200 has first and second parallel elongate channels 206, 208 extending therethrough, and FIGS. 4A and 4B illustrate openings 206o, 208o leading to the first and second channels 206, 208, respectively. The elongate channels 206, 208 are positioned adjacent to one another and their longitudinal axes A1, A2 are parallel to one another. The elongate channels 206, 208 can be discrete and separate channels. In some embodiments, the elongate channels 206, 208 can have the same diameter, which can be, for example, about 0.25 inches. However, a person skilled in the art will appreciate that the elongate channels can have a diameter greater or less than 0.25 inches, and that channels 206, 208 need not have the same diameter.

It should be appreciated that, as used herein, and unless otherwise specified, the terms "first" and "second" are used to differentiate between the elongate channels or other components so defined, and not to indicate any particular order of the components.

In some implementations, the cannula 200 can be at least partially transparent. Furthermore, additionally or alternatively, outer walls of the first and second elongate channels 206, 208 can have one or more openings or windows formed to enable observation of the interior of the channels, and a positon of an instrument introduced into the channel(s). For example, a window can be formed through the wall of each of the channels in proximity to a distal end of the channel. The window can be covered by a transparent or partially transparent material, or it may not be covered and be in the form of an opening.

The proximal handle 204 can have a variety of configurations. In the embodiments described herein, the handle 204 can be a pistol grip-type element that is attached to the cannula 200 at an angle α relative to the longitudinal axes A1, A2 of the channels, as indicated in FIG. 4A. In some embodiments, the angle α can be from about 40 degrees to about 65 degrees, which can allow maneuvering the cannula by holding the handle 204 without obstructing the field of vision. However, the handle 204 can be disposed at other angles with respect to the cannula 200. In the described embodiments, the handle 204 can be non-movably coupled to the cannula 200. In use, the handle 204 can be manipulated so as to change a position of the cannula 200. A person skilled in the art will appreciate that the handle 204 can be integrally formed with the cannula 200, or it can be removably attached to the cannula.

Figure 5:
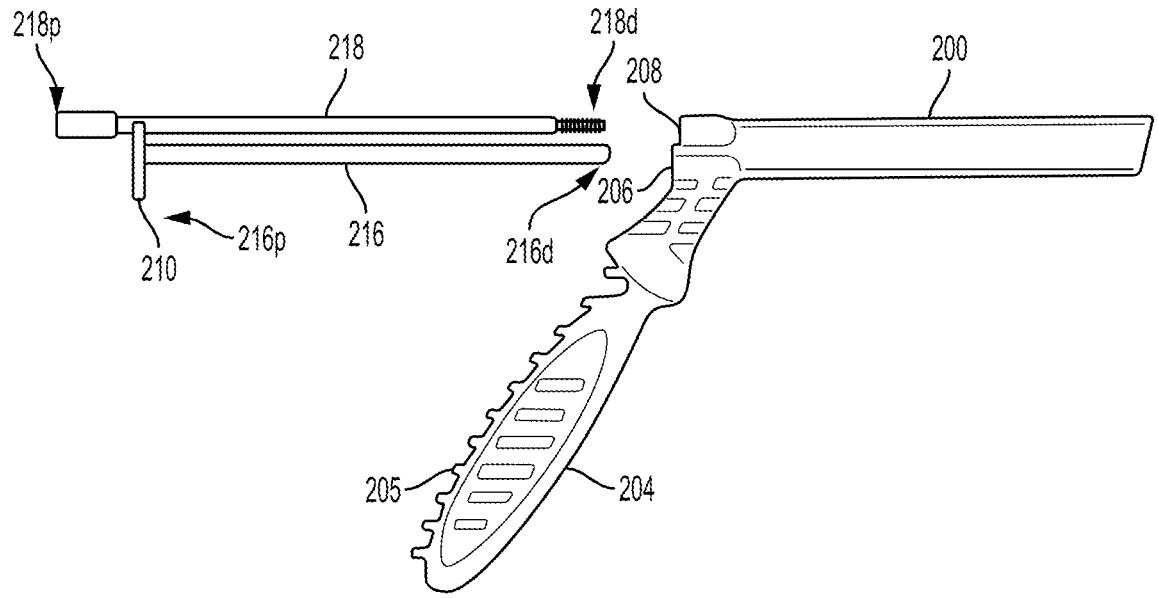
FIG. 5 is a perspective view of the cannula of FIG. 4A and first and second elongate sleeves configured to be received in the first and second elongate channels of the cannula.
Figure 6:
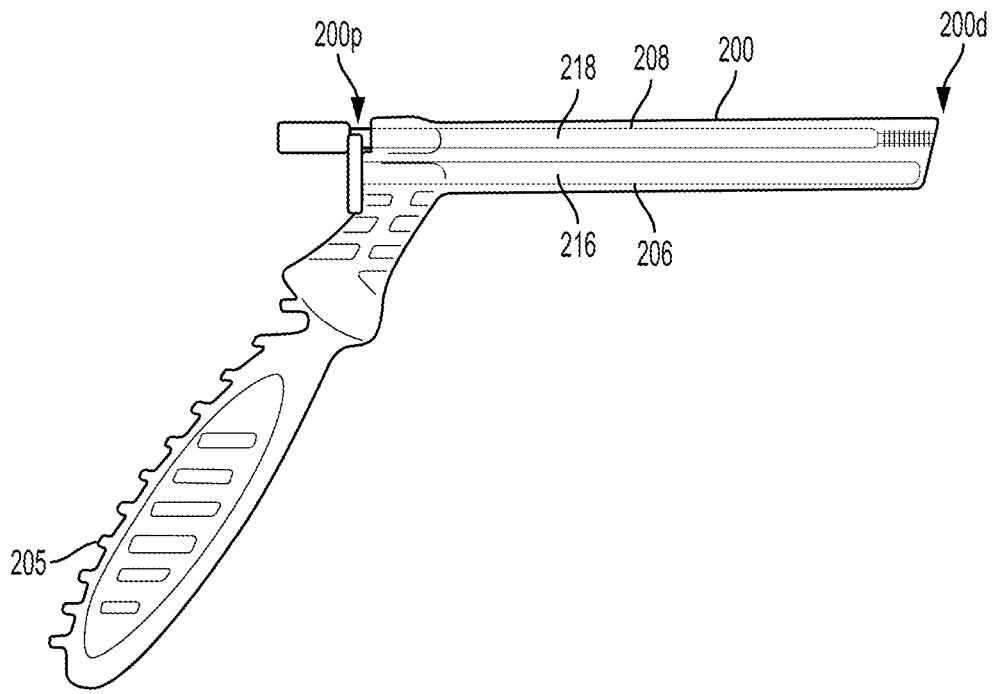
FIG. 6 is a perspective view of the cannula of FIG. 5, showing the first and second elongate sleeves received in the first and second elongate channels.

The proximal handle 204 can be configured to provide an adequate grip, and thus it can have surface features that facilitate grasping and manipulating the device. In the example illustrated, the handle 204 is generally cylindrical, although it has features such that its diameter varies along its length. For example, as shown in FIG. 4A, the handle 204 can have a longer proximal portion 204p and a shorter distal portion 204d coupled to the cannula 200. As shown, the proximal portion 204p has an enlarged mid-portion and has ridges 205 that facilitate grip, which are also shown in FIGS. 5 and 6. The ridges 205 can form various patterns on the handle's surface. The distal portion 204d, which also has ridges similar to the ridges 205, has a bulge-like portion 207a adjacent to the proximal portion 204p, and a distally tapered portion 207b having a smaller diameter than the portion 207a. As a person skilled in the art will appreciate, the handle 204 can have any suitable surface features, including the same or different features, which can form regular or irregular patterns on the handle's surface.

In the illustrated embodiments, the first and second elongate channels 206, 208 of the cannula 200 are configured to receive therein respective first and second elongate sleeves that can be fully cannulated and, in turn, have one or more wire-receiving lumens extending therethrough. Thus, as shown in FIGS. 5 and 6, the first and second elongate channels 206, 208 of the cannula 200 can accommodate respective first and second elongate sleeves 216, 218 removably and replaceably received therein. FIG. 5 illustrates the first and second elongate sleeves 216, 218 outside of the first and second elongate channels 206, 208. As shown, the first and second first and second elongate sleeves 216, 218 have respective proximal ends 216p, 218p and respective distal ends 216d, 218d that are passed through openings of the elongate channels 206, 208 before the proximal ends 216p, 218p when the sleeves 216, 218 are inserted into the channels 206, 208.

FIG. 6, showing the cannula 200 transparent for illustrative purposes only, illustrates the first and second sleeves 216, 218 received within the first and second elongate channels 206, 208, respectively. The first and second elongate sleeves 216, 218 can be removably and replaceably disposed in the first and second elongate channels 206, 208 via a clearance fit. As shown, the proximal end 216p of the first sleeve 216 is configured to protrude from the proximal end 200p of the cannula 200 when the first sleeve 216 is positioned therein. Similarly, the proximal end 218p of the second sleeve 218 is configured to protrude from the proximal end 200p of the cannula 200 when the second sleeve 218 is positioned therein. Furthermore, in some embodiments, the distal ends 216d, 218d of the first and second sleeves 216, 218 can extend beyond the distal end 200d of the cannula 200 when the first and second sleeves 216, 218 are positioned within the cannula 200.

The first and second elongate sleeves 216, 218 can have various different configurations. As shown in FIGS. 5 and 6, the second sleeve 218 can have a greater length than the first sleeve 216 such that the second elongate sleeve 218 can extend more proximally beyond the proximal end 200p of the cannula 200 than the first elongate sleeve 216. Also, in the illustrated embodiments, the first and second sleeves 216, 218 have different configurations, as also shown in FIGS. 7A-7C and FIGS. 8A and 8B. For example, the proximal end 216p of the first elongate sleeve 216 can have a washer-like shape, whereas the proximal end 218p of the second elongate sleeve 218 can be more elongate and having a diameter than is less than a diameter of the washer-like the proximal end 216p of the first elongate sleeve 216. Furthermore, while the second sleeve 218 has one wire-receiving lumen extending therethrough, the first sleeve 216 has more than one wire-receiving lumen, as discussed in more detail below.

Figure 7A:
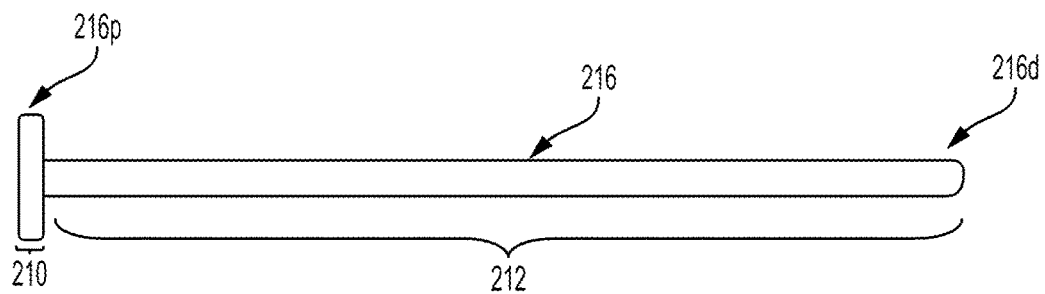
FIG. 7A is a perspective view of one embodiment of a first elongate sleeve.

As shown in FIGS. 5, 6, and 7A, the first elongate sleeve 216, which is configured to be removably and replaceably received in the first channel 206, a proximal housing 210 configured to protrude from the proximal end 200p of the cannula 200. The proximal housing 210 has a generally circular cross-section, although it can have other features such that the contour of the cross-section is only partially circular along a perimeter of the cross-section. Furthermore, in other implementations, the proximal housing 210 can have other configurations such that its cross-sectional shape is not circular.

As shown in FIGS. 5, 6, and 7A, the proximal housing 210 has a diameter that is larger than a diameter of an elongate tubular body 212 of the first elongate sleeve 216 that extends distally from the housing 210. The diameter of the housing 210 is also larger than a diameter of the opening 206o leading to the first channel 206 of the cannula 200, such that the housing 210 extends beyond the proximal end 200p of the cannula 200 when the first sleeve 216 is inserted into the first channel 206 in the cannula 200.

Figure 7B:
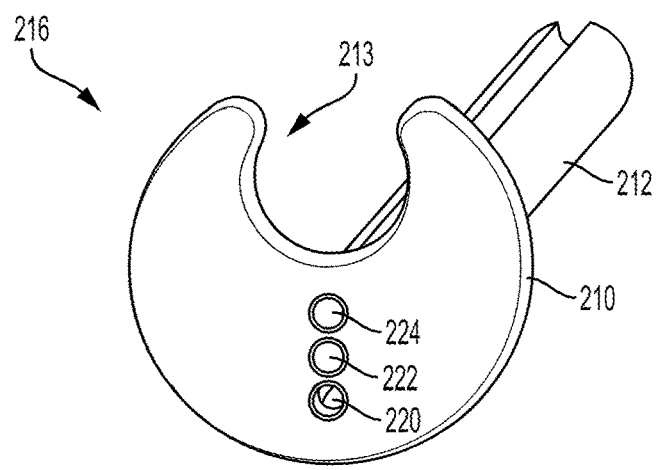
FIG. 7B is another, enlarged perspective view of the first elongate sleeve of FIG. 7A, illustrating openings in a proximal end of the sleeve.
Figure 7C:
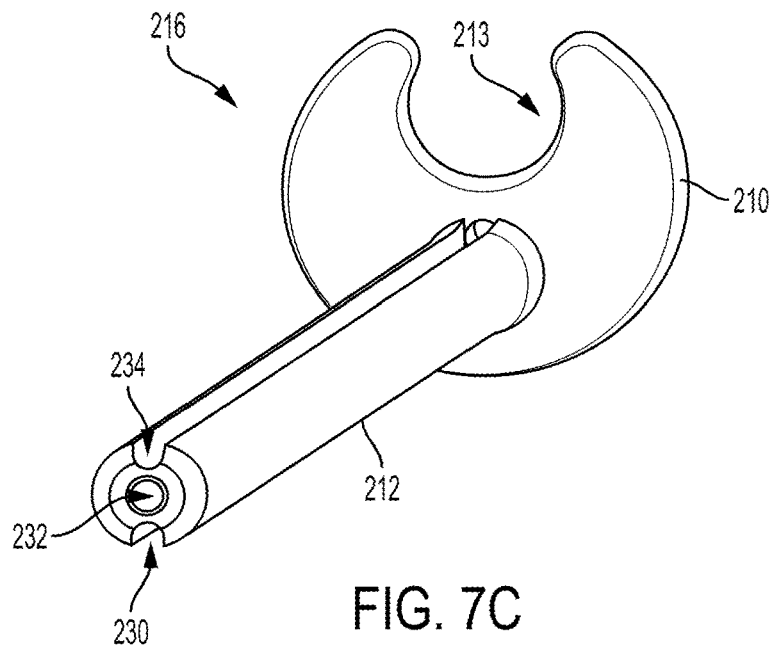
FIG. 7C is another, enlarged perspective view of the first elongate sleeve of FIG. 7A, illustrating wire-receiving lumens extending through the sleeve.

As shown in FIG. 7B, the proximal housing 210 of the first elongate sleeve 216 has three openings 220, 222, 224 formed therein. Each of the first, second, and third openings 220, 222, 224 is in communication with a respective one of first, second, and third wire-receiving lumens or channels 230, 232, 234 that extend through the first elongate sleeve 216 to the distal end 216d thereof. The wire-receiving lumens 230, 232, 234, each configured to receive a wire (e.g., a Kirschner or K-wire or other wires) therethrough, extend through the first elongate sleeve 216 such that their respective longitudinal axes are disposed in the same plane, as shown in FIG. 7C. In the illustrated example, as also shown in FIG. 7C, the second wire-receiving lumen 232 disposed between the first wire-receiving lumen 230 and the third wire-receiving lumen 234 is a completely enclosed lumen, whereas each of the first and third lumens 230, 234 have a longitudinal portion of its walls open. It should be appreciated, however, that all of the wire-receiving lumens 230, 232, 234 can be completely enclosed, or the configurations of the walls of the lumens 230, 232, 234 can vary in other ways.

The proximal housing 210 of the first elongate sleeve 216 can have other features. For example, in the example illustrated, the proximal housing 210 has a coupling element that allows reversible coupling of the first elongate sleeve 216 to the second elongate sleeve 218 such that independent rotation of the first and second sleeves 216, 218 is not possible. Thus, as shown in FIGS. 7B and 7C, the proximal housing 210 has an arcuate slot 213 configured to receive therein a portion of the proximal end 218p of the second elongate sleeve 218 such that independent rotation of the first and second elongate sleeves 216, 218 is not possible. It should be appreciated that the proximal housing 210 can have other features not shown herein.

Figure 8A:
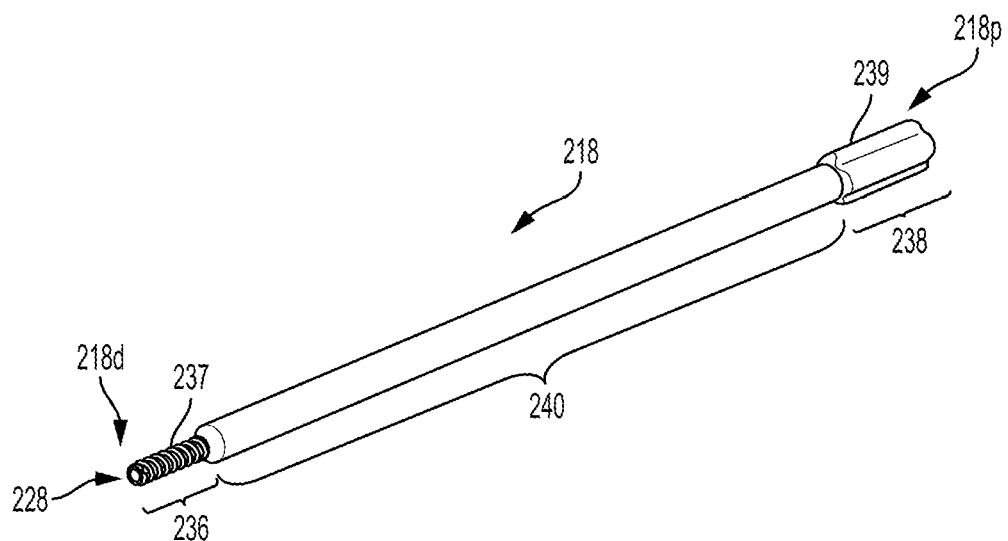
FIG. 8A is a perspective view of one embodiment of a second elongate sleeve.
Figure 8B:
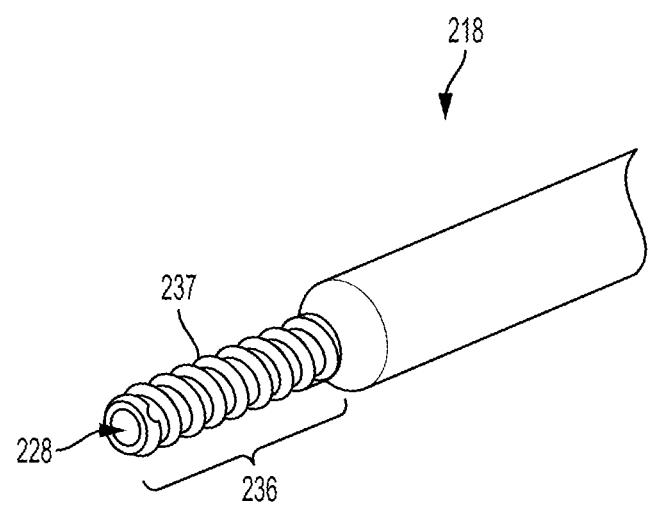
FIG. 8B is an enlarged perspective view of a distal end of the second elongate sleeve of FIG. 8A.

As shown in FIGS. 8A and 8B, the second elongate sleeve 218, the second elongate sleeve 218, configured to be removably and replaceably received in the second channel 208, has a wire-receiving lumen 228 extending therethrough. In the example illustrated, the distal end 218d of the second elongate sleeve 218 has a threaded portion 236 with a thread 237 formed therearound, like in the example illustrated. The thread 237 can be useful for other steps of a surgical procedure that are not relevant to this disclosure. The proximal end 218p of the second elongate sleeve 218 has an elongate portion 238 having several elongate arcuate protrusions 239 extending along a longitudinal axis of the second elongate sleeve 218, as shown in FIG. 8A. Although four or less protrusions 239 are shown, the number of protrusions 239 is not critical and any number of protrusions can be present. The protrusions 239 can facilitate grasping and manipulating sleeve 218 and, like the threaded proximal portion 236, can be useful for other aspects of a surgical procedure that are neither relevant nor described herein.

An elongate tubular mid-portion 240 of the second elongate sleeve 218 extending between the proximal and distal ends 218p, 218d can have a diameter than is greater than a diameter of the distal end 218p and smaller than a diameter of the proximal end 218p, as shown in FIG. 8A. A distal end of the elongate mid-portion 240 can be tapered distally, as shown in FIGS. 8A and 8B. It should be appreciated that the specific configuration of the second elongate sleeve 218 is shown herein by way of example only, as the second elongate sleeve 218 can have other various configurations.

Referring back to FIGS. 7B and 7C, in the illustrated embodiments, the first elongate sleeve 216 is configured so as to define an offset between one of its wire-receiving lumens 230, 232, 234 and the wire-receiving lumen 228 extending through the second elongate sleeve 218. Specifically, each of the three openings 220, 222, 224 defines a different offset distance between the wire-receiving lumen in communication with that opening and the wire-receiving lumen 228 of the second elongate sleeve 218. For example, the first, second, and third openings 220, 222, 224 can define offset distances of about 11 mm, about 9 mm, and about 7 mm, respectively. A person skilled in the art will appreciate, however, that the openings in the first elongate sleeve 216 can define various offset distances (including those other than about 11 mm, about 9 mm, and about 7 mm), as embodiments are not limited to any specific offsets. Furthermore, two or more than three openings leading to corresponding lumens can be formed in the first elongate sleeve 216.

Regardless of the number of the openings in the first elongate sleeve 216 and offsets defined by the openings, in use, each offset is used to define a respective offset of openings to be formed in the bone. For example, an offset of an opening in a glenoid from a glenoid rim can thus be defined, as discussed in more detail below.

Figure 9:
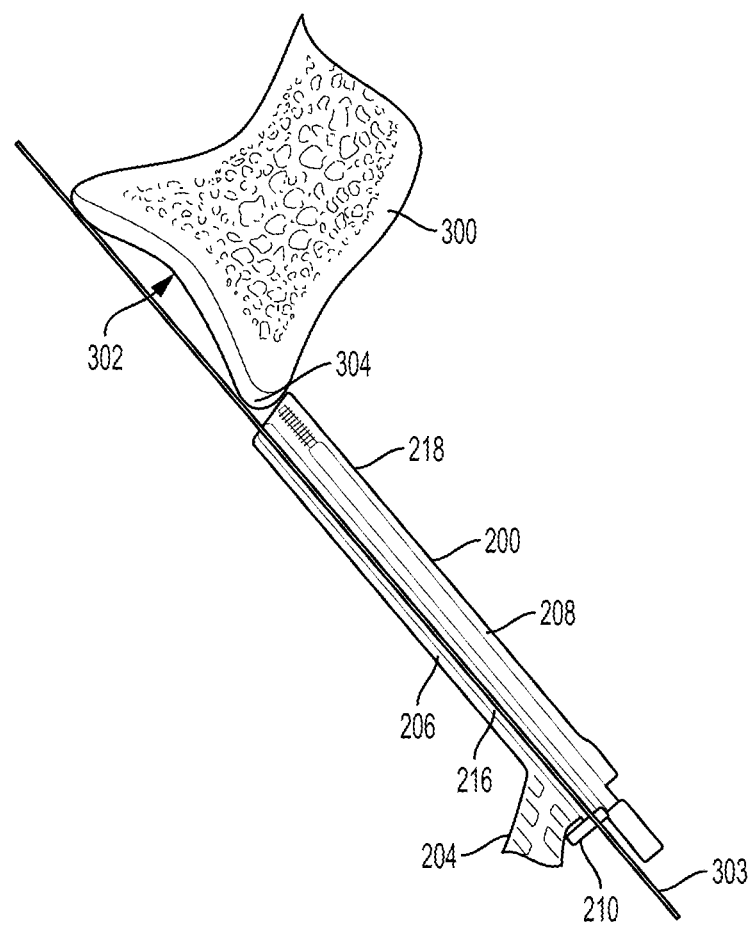
FIG. 9 is a perspective view of one embodiment of a surgical guide device, illustrating the surgical guide device positioned adjacent to a glenoid during a bone reconstruction procedure.

FIG. 9 illustrates schematically a way in which the cannula 200 can be positioned initially to prepare a bone, such as a glenoid 300 of a shoulder joint, for a surgical procedure involving placement of a graft bone to the glenoid 300. As shown, the cannula 200 can be positioned along the glenoid anterior surface 302 (sometimes referred to herein as the "end surface") of the glenoid 300 defining the glenoid cavity such that it abuts a glenoid rim 304. As discussed above, the cannula 200 has the first and second parallel elongate channels 206, 208 extending therethrough that have the first and second sleeves 216, 218 received therein, respectively. The proximal handle 204 coupled to the cannula 200 is also shown partially in FIG. 9. As also shown in FIG. 9, a first wire 303 is positioned in the lumen of the first sleeve 216 disposed such that the first wire 303 extends along a plane defined by the end surface 302 of the glenoid 300. The method for preparing a bone, including subsequent steps not illustrated in FIG. 9, is described in more detail below in connection with FIGS. 10A-10F.

FIGS. 10A-10F illustrate an exemplary implementation of a method for preparing a bone, such as the glenoid 300 of a right shoulder joint 301 shown partially in FIGS. 10A-10F, for a surgical procedure, in accordance with the described techniques. The method involves using a cannula 400 which is generally similar to cannula 200 (FIGS. 4A and 4B). The method is performed to define first and second openings in the glenoid 300 configured to receive therein bone screws for attaching a bone graft to the glenoid 300.

A surgery for which the bone can be prepared in accordance with the described techniques can be, for example, an arthroscopic bone transplanting procedure for treatment of an anterior shoulder instability, where a portion of a coracoid is transplanted to a glenoid. An example of such a surgery, as well as instruments that can be used during the surgery (which are not described herein), are described in U.S. Pat. No. 8,617,219 entitled "Arthroscopic Bone Transplanting Procedure, And Medical Instruments Useful Therein," and filed Nov. 6, 2009, which is hereby incorporated by reference in its entirety.

Figure 10A:
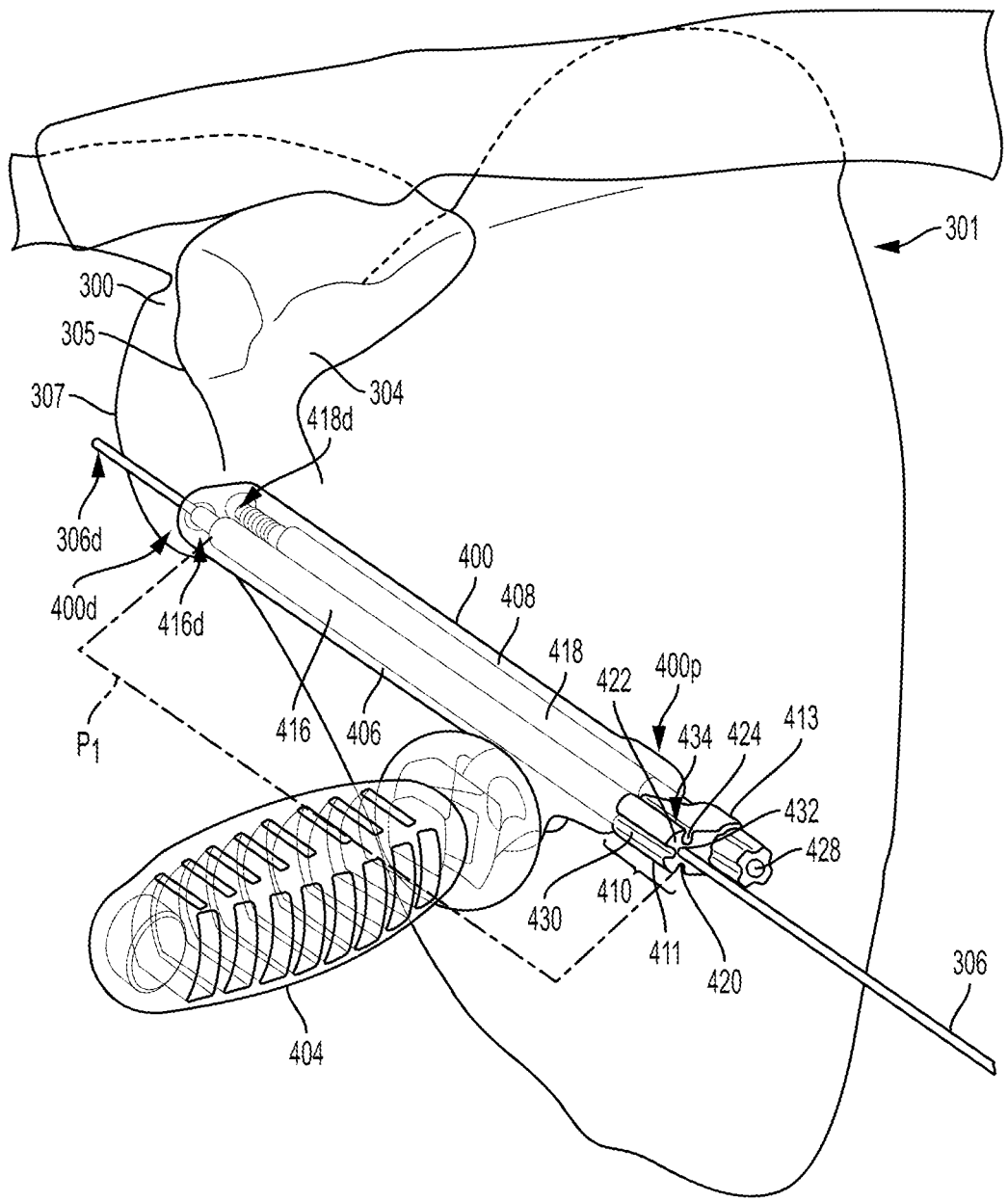
FIGS. 10A-10F illustrate one embodiment of a method for preparing a glenoid for a surgical procedure, using one embodiment of a surgical guide device.

A patient (not shown) can be appropriately prepared for the surgery and brought into a suitable position. A surgical site in the patient's shoulder can also be prepared using suitable techniques. The cannula 400 can then be introduced into the shoulder joint and it can be positioned along the end surface 302 of the glenoid 300 defining the glenoid cavity. As shown in FIG. 10A, the cannula 400 is disposed parallel to the glenoid surface such that a distal end 400d of the cannula 400 abuts the glenoid rim 304.

Like the cannula 200, the cannula 400 has first and second parallel elongate channels 406, 408 extending therethrough that have first and second sleeves 416, 418 received therein, respectively. The cannula 400 extends distally from a proximal handle 404 coupled to the cannula 400 at a proximal end 400p of the cannula.

Similar to the proximal housing 210 of the first sleeve 216 received in the cannula 200, a proximal housing 410 of the first sleeve 416 has three openings, each defining a different offset distance and leading to a respective wire-receiving lumen, and a coupling element configured to non-movably couple the first sleeve 416 to the second sleeve 418. However, as shown in FIGS. 10A-10F, the proximal housing 410 has a configuration that differs in some aspects from that of the proximal housing 210 of the first sleeve 216. For example, as indicated in FIG. 10A, the proximal housing 410 has an elongate arcuate portion 411 in which three wire-receiving lumens 430, 432, 434 are formed, and the coupling element 413 extending laterally from the arcuate portion 411 so as to be disposed at least partially around a portion at the proximal end of the second sleeve 418. In the example illustrated, the coupling element 413 is formed integrally and/or monolithically with the arcuate portion 411 of the proximal housing 410. However, in other implementations, the coupling element can be a separate element that can be coupled to one or both of the first and second sleeves in a suitable manner so as to prevent rotation of the sleeves with respect to one another.

The coupling element 413 is in the form of a semi-arcuate bracket having arms sized so as to receive the portion of the second sleeve 418 between the arms. The bracket can be configured to reversibly snap over the second sleeve 418, or it can be configured to be otherwise attached to the second sleeve 418. It should be appreciated that the coupling element can have other configurations, as embodiments described herein are not limited to any specific feature(s) used to reversibly couple the first and second sleeves so as to prevent their rotation with respect to one another. Also, the coupling element can alternatively be formed on the second sleeve, or it can be a separate element configured to couple the first and second sleeves.

In the example of FIGS. 10A-10F, the distal end 416d of the first sleeve 416 is in the form of a threaded portion. However, like the distal end of the first sleeve 216 (FIGS. 5, 6, and 7A), the distal end 416d of the first sleeve 416 can lack the threaded portion. Other configurations of the distal end, as well as other portions of the first sleeve 416, can be implemented additionally or alternatively.

Openings 420, 422, 424 formed in the proximal housing 410 of the first sleeve 416, each defining a different offset distance, lead to the respective wire-receiving lumens 430, 432, 434, as shown in FIG. 10A. The middle opening 422 leads to the wire-receiving lumen 432 in the form of an enclosed lumen. The openings 420, 424 are in the form of proximal ends of the wire-receiving lumens 430, 434 each of which has a portion of its wall open along the longitudinal axis of the lumen.

The second sleeve 418 configured to be received in the second channel 408 in the cannula 400 is configured similarly to the second sleeve 218 received in the cannula 200. The second sleeve 418 has a wire-receiving lumen 428 extending therethrough, as shown in FIG. 10A.

Referring back to the method of preparing the glenoid 300 for a graft placement procedure, as shown in FIG. 10A, the cannula 400 is positioned along the end surface 302 of the glenoid 300 such that the first and second elongate channels 406, 408 are disposed in a first plane schematically shown as a plane P1. The cannula 400 abuts the glenoid rim 304.

Once the cannula 400 is properly positioned, a first wire 306 is positioned in the lumen of the first sleeve 416 disposed in the first channel 406 such that the first wire 306 extends along a plane defined by the end surface 302 of the glenoid 300, as shown in FIG. 10A. A distal end 306d of the first wire 306 can be blunt to avoid damage to cartilage. The first wire 306 can be a K-wire or other removable elongate element.

The first wire 306 is inserted into one of the plurality of openings formed in the first sleeve 416 to thereby define a desired offset distance between the respective wire-receiving lumen in the first sleeve 416 and the wire-receiving lumen extending through the second sleeve 418. In the example of FIGS. 10A-10F, the first wire 306 is shown by way of example only as being introduced into a middle opening 422. However, a person skilled in the art will appreciate that the first wire 306 can be introduced into any of the openings formed at a proximal end 416p of the first sleeve 416, depending on a desired offset distance of openings to be formed in the glenoid from the edge 305 of the glenoid rim 304.

Regardless of which one of the openings in the first sleeve 416 receives the first wire 306, the first wire 306 in placed in front of the glenoid and advanced through tissue across the glenoid end surface 302, such that it is ultimately positioned against the farther edge 307 of the glenoid 300, as shown in FIG. 10A. When the cannula 400 is disposed adjacent to the glenoid during the bone preparation procedure, the first sleeve 416 is positioned such that the first wire 306 extending therethrough does not penetrate the bone and extends along the surface of the glenoid. At the same time, as shown in FIG. 10A, a distal end 418d of the second sleeve 418 abuts the glenoid rim 304. The first wire 306 is pressed against the glenoid surface, and it is "pinned" in place, without penetrating the bone, such that it serves to mark the location of the surface 302 of the glenoid.

Figure 10B:
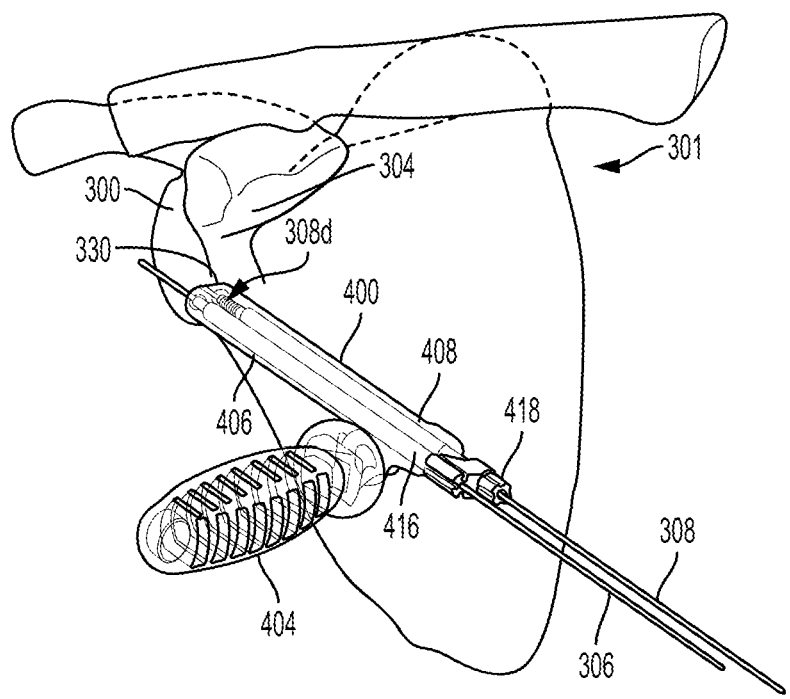

After the first wire 306 is received in the first sleeve 416, a second wire 308 is positioned in the wire-receiving lumen 428 of the second sleeve 418 that is received in the second channel 408, as shown in FIG. 10B. Similar to the first wire 306, the second wire 308 can be a K-wire or other removable elongate element. The second wire 308 is advanced distally through sleeve 418 such that a distal end 308d of the second wire 308 is inserted into a portion of the glenoid 300 spaced away from the end surface 302 to define the location of a first opening 330 in the glenoid 300. The second wire 308 can be inserted (e.g., drilled) into the glenoid 300 to a relatively small distance, e.g., it can be inserted to a depth of about 5 mm into the glenoid bone. It should be appreciated that the second wire 308 can be inserted to other depths within the glenoid bone. Regardless of the specific depth to which the second wire 308 is advanced through the glenoid, in this way, the location of the first opening 330 in the glenoid 300 is defined.

Figure 10C:
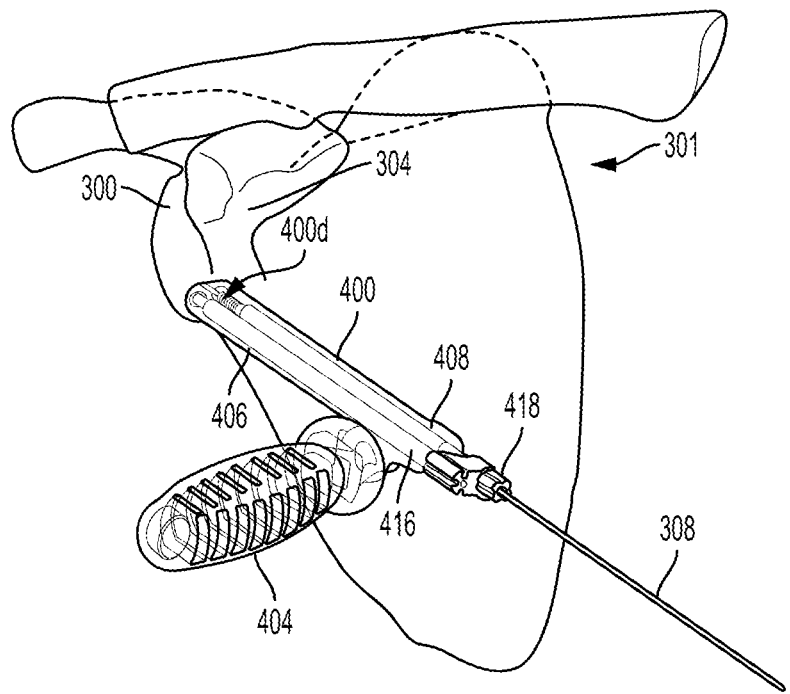

After locating the position of the first opening 330 in the glenoid 300 is defined as indicated above, the first wire 306 is at least partially retracted from the first sleeve 416 in the first channel 406 so as to move some distance away from the glenoid 300, such that the distal end thereof does not protrude from the distal end 400d of the cannula 400. In the example illustrated, as shown in FIG. 10C, the first wire 306 is completely removed from the first channel 406.

Figure 10D:
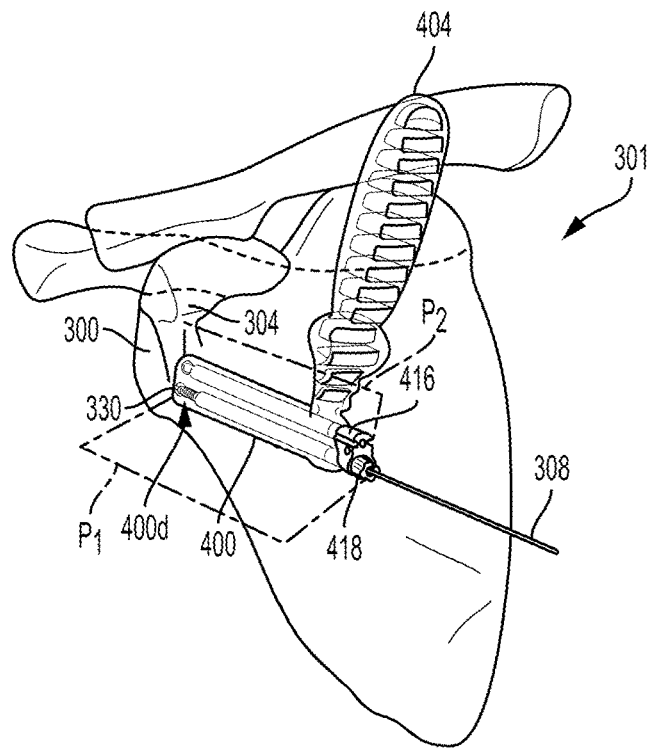

After the first wire 306 is at least partially retracted from the first channel 406, and while the second wire 308 remains in place, the cannula 400 is rotated about the second wire 308, as shown in FIG. 10D. Such rotation can be effected by manipulating the handle 404 such that the handle 404 is moved in the "up" direction (as shown in FIGS. 10C and 10D) and the cannula 400 is aligned with the glenoid surface. Following this rotation of the first and second elongate channels 406, 408 are disposed in a second plane P2 that is substantially perpendicular to the first plane P1, as shown in FIG. 10D. The cannula 400 is rotated about the second wire 308 until the distal end of the first sleeve 416 abuts the glenoid.

Figure 10E:
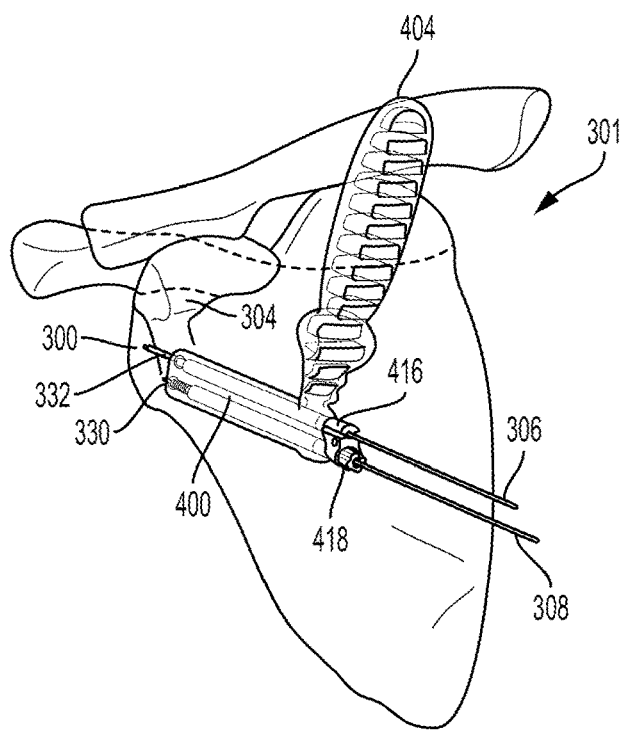
Figure 10F:
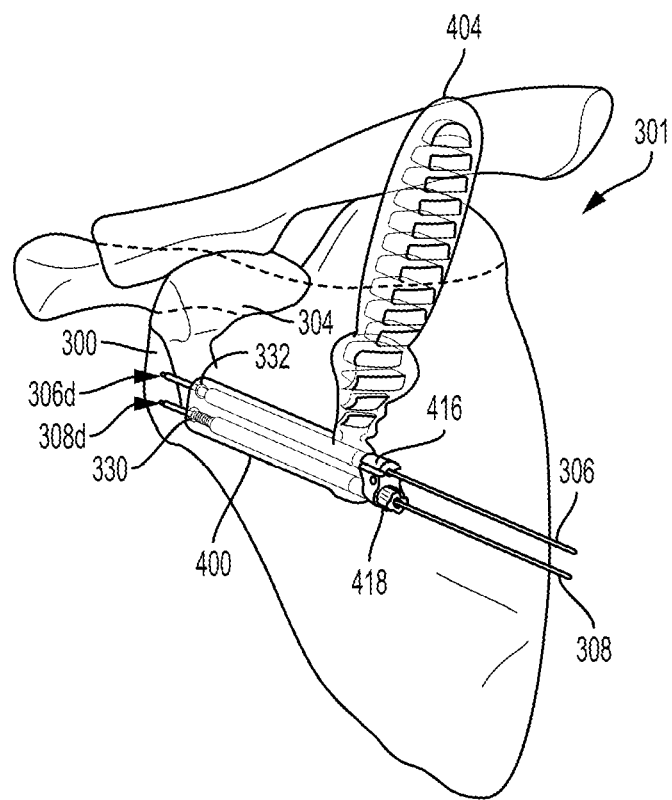

After the cannula 400 is rotated and while it remains in the position shown in FIG. 10D, the first wire 306 is again inserted into the first sleeve 416, positioned within the first channel 406, and advanced distally until it is inserted through the glenoid 300 to thereby define the location of a second opening 332 in the glenoid 300, as shown in FIG. 10E. The first wire 306 can be drilled completely through the glenoid. The second wire 308 can be inserted to an increased depth into the glenoid such that its distal end 308d is disposed more distally, as shown in FIG. 10F. In this way, both the first and second openings 330, 332 in the glenoid 300 are formed.

Figure 11:
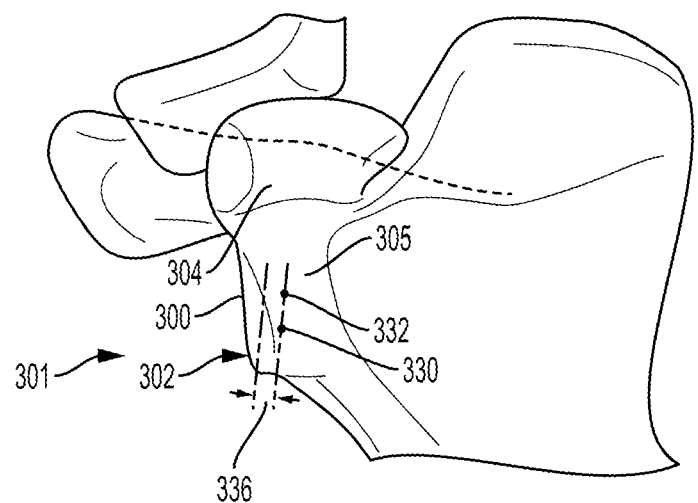
FIG. 11 illustrates the glenoid prepared for a surgical procedure using the method of FIGS. 10A-10F.
Figure 12:
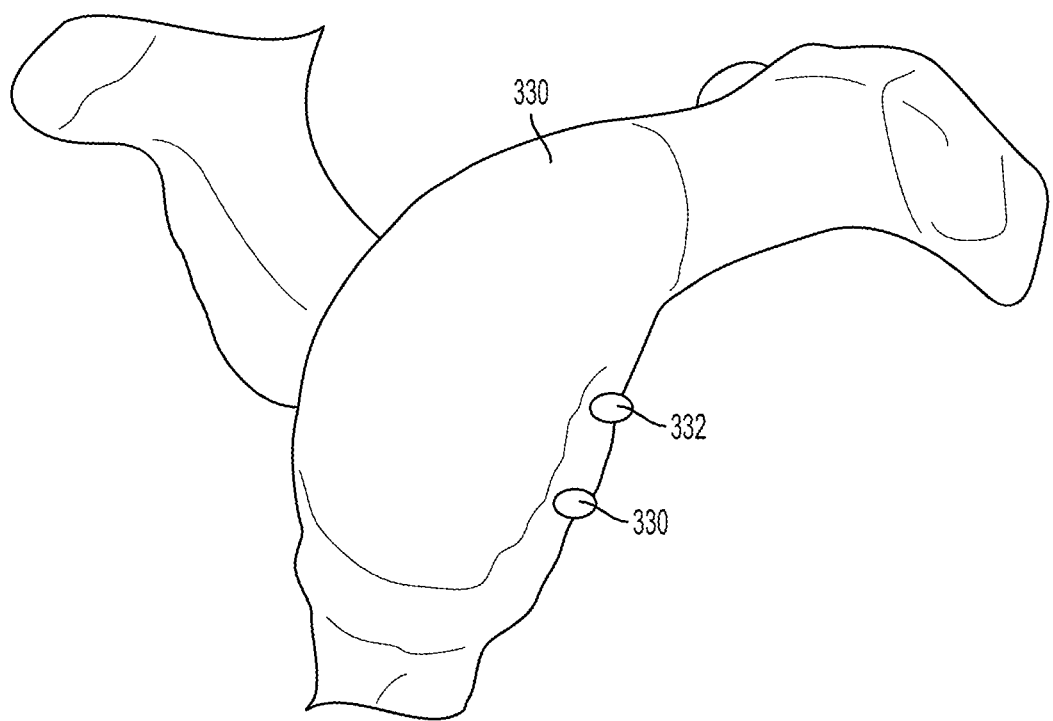
FIG. 12 illustrates openings for bone screws defined in a glenoid prepared for a surgical procedure using a method in accordance with the described embodiments.

FIG. 11 illustrates the first and second openings 330, 332 formed at a specified 336 offset distance from the edge 305 of the glenoid rim 304. FIG. 12 additionally shows the glenoid 300 with the openings 330, 332 formed therein.

After the first and second openings are formed, they can be widened using a suitable instrument (e.g., a drill or other bone cutting instrument) such that they are appropriately dimensioned to receive respective first and second bone screws therein. A bone graft can be acquired by known surgical techniques, for example, similar to the technique shown in connection with FIGS. 1A and 1B. As discussed above, a coracoid can be osteotomized (e.g., using an osteotome or other cutting tool) using an approach as known in the art to form a coracoid bone graft having a tendon attached thereto.

The coracoid bone graft can be placed over the first and second wires extending through the cannula, and the bone graft can be attached to the glenoid 300 using first and second screws.

It should be appreciated that, although not described herein, various other instruments can be used during the surgical procedure, examples of which are described in U.S. Pat. No. 8,617,219 entitled "Arthroscopic Bone Transplanting Procedure, And Medical Instruments Useful Therein," and filed Nov. 6, 2009, which is hereby incorporated by reference in its entirety.

It should also be appreciated that the surgical guide device described herein can have any number of variations. For example, in some embodiments, the cannula, such as cannula 200 (FIGS. 4A and 4B) or cannula 400 (FIGS. 10A-10E), or a similar cannula, can be formed such that the first elongate channel and the first elongate sleeve are not separate elements but are rather formed as one component. The second elongate channel and second first elongate sleeve can similarly be formed as one component. In such cases, the first and second elongate sleeves can be configured to be non-removably received in the first and second channels, respectively. As another variation, the first and second elongate sleeves can be integrally and/or monolithically formed with the first and second channels, respectively.

The techniques described herein can be used to position a bone graft adjacent to the bone, such as the glenoid or other bone structure, to compensate for the bone deficit in the bone such that the surface of the bone graft is flush with the surface of the bone. Thus, certain shortcomings associated with the conventional Latarjet surgery can be alleviated. Specifically, because the openings in the bone are formed in the straightforward manner, the reliance on a surgeon's experience is reduced. As a result, a possibility of an incorrect positioning of the bone graft with respect to the bone, and thus of the associated damage to the bone, is greatly decreased or even completely eliminated. Thus, when the bone is prepared as described herein, this contributes to the successful outcome of the surgery.

It should be appreciated that the described techniques can be used for preparing a bone to receive a bone graft as part of a number of different procedures. For example, a bone can be prepared for a Bristow procedure or its variants, a Trillat procedure for recurrent anterior instability of the shoulder, or any other procedure, including anterior and posterior bone bloc procedures. Also, although the illustrated embodiments provide techniques for preparing a glenoid for a shoulder joint reconstruction surgery, the techniques can be adapted for preparation of other bones as well.

A bone graft can be any suitable graft. For example, it can be, as in the embodiments described above, an autograft, which is a patient's own bone with the tendon coupled thereto that would replace the damaged portion of another bone. The bone graft can also be obtained from a donor ("allograft"). The graft can be an iliac crest bone graft, or any other graft.

Furthermore, although the illustrated embodiments provide techniques for preparing a bone for receiving a bone graft in a surgical procedure, the techniques can be used for other surgical procedures as well. For example, the techniques can be used for placing an implant at a certain desired distance from an edge of a bone. In such cases, the implants can be used to reattach soft tissues to the bone. As another example, the described techniques can be used for a trauma reconstruction surgery to place an implant, intended to fix a fracture or other trauma, at a certain distance from an edge of a bone. It should be further appreciated that the described techniques can be used to prepare a bone for any other procedure.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices and components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the described techniques based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical method, comprising:
preparing a glenoid for a bone graft placement procedure by forming, using a surgical guide device, first and second non-intersecting openings in the glenoid at a predefined offset relative to one another;
wherein the surgical guide device includes a first elongate sleeve having a plurality of lumens extending therealong, and includes a second elongate sleeve having a single lumen extending therealong;
a location of the first opening is defined by which one of the plurality of lumens a first fixation element is advanced through to contact the glenoid; and
a location of the second opening is defined by the first fixation element again being advanced through the one of the plurality of lumens to contact the glenoid.

2. The method of claim 1, wherein forming the first opening includes, with the first fixation element contacting the glenoid, advancing a second fixation element through the single lumen of the second elongate sleeve to contact the glenoid;
forming the second opening includes, with the second fixation element contacting the glenoid, the first fixation element again being advanced through the one of the plurality of lumens to contact the glenoid.

3. The method of claim 2, wherein the surgical guide device is rotated relative to the glenoid between the forming of the first opening and the forming of the second opening.

4. The method of claim 3, wherein the surgical guide device is rotated about the second fixation element that is contacting the glenoid.

5. The method of claim 4, wherein the second elongate sleeve is releasably coupled to a coupling element of the first elongate sleeve so as to prevent rotation of the second elongate sleeve relative to the first elongate sleeve.

6. The method of claim 2, further comprising placing the bone graft over the first and second fixation elements and attaching the bone graft to the glenoid.

7. The method of claim 1, wherein the first elongate sleeve is slidably positioned in a first elongate channel of the surgical guide device during the advancing of the first fixation element;
the second elongate sleeve is slidably positioned in a second elongate channel of the surgical guide device during the advancing of the first fixation element; and
the first elongate channel is parallel to the second elongate channel.

8. The method of claim 1, wherein the first and second fixation elements are each a wire.

9. A surgical method, comprising:
positioning a surgical guide device relative to a scapula such that the surgical guide device abuts a first portion of the scapula;
with the surgical guide device abutting the scapula, defining a location of a first opening in the scapula using a first wire advanced through the surgical guide device into contact with the scapula;
after defining the location of the first opening in the scapula and with the first wire in contact with the scapula, rotating the surgical guide device relative to the scapula such that the surgical guide device abuts a second portion of the scapula that is at a distance from the first portion of the scapula; and
after rotating the surgical guide device, defining a location of a second opening in the scapula using a second wire advanced through the surgical guide device into contact with the scapula.

10. The method of claim 9, wherein the first and second openings are at an offset from one another that is defined by openings formed in the surgical guide device.

11. The method of claim 9, further comprising, before advancing the first wire through the surgical guide device to define the location of the first opening, advancing the second wire into a selected one of a plurality of openings formed in the surgical guide device and advancing the second wire through the surgical guide device and into contact with the scapula; and
before rotating the surgical guide device, retracting the second wire.

12. The method of claim 11, wherein the surgical guide device is rotated about the first wire.

13. The method of claim 11, wherein the selected one of the plurality of openings defines an offset between the first and second openings in the scapula.

14. The method of claim 9, wherein the first wire is advanced through a first elongate sleeve of the surgical guide device located in a first elongate channel of the surgical guide device;
the second wire is advanced through a second elongate sleeve of the guide located in a second elongate channel of the surgical guide device; and
the first and second elongate channels are parallel.

15. The method of claim 9, wherein the surgical guide device is rotated about the first wire.

16. The method of claim 9, wherein the first and second openings are parallel to one another.

17. The method of claim 9, further comprising placing a bone graft over the first and second wires and attaching the bone graft to the scapula.

18. The method of claim 9, wherein the first and second openings are defined in a glenoid.

19. A surgical method, comprising:
advancing a first wire through a selected one of a plurality of lumens extending through a first elongate sleeve removably and replaceably received in a first elongate channel of a cannula such that the first wire contacts a glenoid to prepare a first opening in the glenoid to receive a bone graft; and
advancing a second wire through a lumen of a second elongate sleeve such that the second wire contacts the glenoid to prepare a second opening in the glenoid to receive the bone graft, the lumen of the second elongate sleeve being the only lumen extending through the second elongate sleeve, the second elongate sleeve being removably and replaceably received in a second elongate channel of the cannula that is parallel to the first elongate channel, and the second elongate sleeve being removably and replaceably coupled to a coupling element in a proximal portion of the first elongate sleeve that is located proximal to the cannula.

20. The method of claim 19, further comprising, after advancing the first wire and before advancing the second wire, and with the first elongate sleeve removably and replaceably received in the first elongate channel and the second elongate sleeve being removably and replaceably received in the second elongate channel, rotating the cannula relative to the glenoid.

* * * * *